US00RE38972E

(19) United States
(12) Reissued Patent
Purdy

(10) Patent Number: US RE38,972 E
(45) **Date of Reissued Patent: *Feb. 7, 2006**

(54) INTRAVASCULAR DEVICE

(75) Inventor: Phillip D. Purdy, Dallas, TX (US)

(73) Assignee: Board of Regents, The University of Texas System, Austin, TX (US)

( * ) Notice: This patent is subject to a terminal disclaimer.

(21) Appl. No.: 09/909,662

(22) Filed: Jul. 19, 2001

Related U.S. Patent Documents

Reissue of:
(64) Patent No.: 5,925,062
Issued: Jul. 20, 1999
Appl. No.: 08/938,081
Filed: Sep. 26, 1997

(60) Division of application No. 08/662,845, filed on Jun. 12, 1996, now Pat. No. 5,693,067, which is a division of application No. 08/164,398, filed on Dec. 9, 1993, now Pat. No. 5,527,338, which is a continuation-in-part of application No. 07/939,296, filed on Sep. 2, 1992, now Pat. No. 5,443,478.

(51) Int. Cl.
*A61B 29/00* (2006.01)

(52) U.S. Cl. ..... 606/200
(58) Field of Classification Search ..... 606/200, 606/151, 157, 114, 113, 127
See application file for complete search history.

(56) References Cited

U.S. PATENT DOCUMENTS 3,540,431 A * 11/1970 Mobim-Uddim
3,794,041 A * 2/1974 Frei et al.
3,868,956 A * 3/1975 Alfidi et al.
4,046,150 A * 9/1977 Schwartz et al. ..... 606/127
4,365,632 A * 12/1982 Kortum
4,425,908 A * 1/1984 Simon
4,447,227 A * 5/1984 Kotsanis
4,494,531 A * 1/1985 Gianturco
4,512,338 A * 4/1985 Balko et al.
4,619,246 A * 10/1986 Molgaard-Nielsen et al.
4,638,803 A * 1/1987 Rand
4,957,501 A * 9/1990 Lahille et al.
4,994,069 A * 2/1991 Ritchart et al.
4,997,435 A * 3/1991 Demeter
5,053,008 A * 10/1991 Bajaj
5,071,407 A * 12/1991 Termin et al.
5,104,404 A * 4/1992 Wolff
5,108,407 A * 4/1992 Geremia et al.
5,108,419 A * 4/1992 Reger et al.
5,217,484 A * 6/1993 Marks
5,250,071 A 10/1993 Palermo ..... 606/198
5,256,146 A * 10/1993 Ensminger et al.
5,261,916 A 11/1993 Engelson ..... 606/108
5,263,964 A * 11/1993 Purdy
5,304,195 A 4/1994 Twyford, Jr. et al. ..... 606/191
5,350,397 A 9/1994 Palermo et al. ..... 606/200
5,443,478 A * 8/1995 Purdy
5,527,338 A * 6/1996 Purdy
5,693,067 A * 12/1997 Purdy

* cited by examiner

*Primary Examiner*—Kevin T. Truong
(74) *Attorney, Agent, or Firm*—Fulbright & Jaworski L.L.P.

(57) ABSTRACT

A multi-element occlusion device (10, 20, 30, 40) provides an improvement over existing systems by increasing the occupation of a vascular lumen. The device (10, 20, 30) comprises an anchoring element (12, 22, 32), a lead element (14, 24, 34) and at least one fiber (16, 26, 36) attaching said elements. The elements and fibers produce a cumulative occlusive effect greater than the sum of the individual elements. When placed in the blood stream, the anchoring element (12, 22, 32) lodges against the vessel wall and the lead element (14, 24, 34) is carried to a position distal thereto. In another embodiment, an "umbrella" of support members extend from the lead element. A fabric web extends between these support members. The umbrella intravascular device expands upon its exit from the catheter. The fabric web produces complete occlusion of the vessel without the need for thrombosis to form between the elements. With the use of multi-element deployment, the device decreases the risk of continued canalization and recanalization.

13 Claims, 5 Drawing Sheets

INTRAVASCULAR DEVICE

Matter enclosed in heavy brackets [ ] appears in the original patent but forms no part of this reissue specification; matter printed in italics indicates the additions made by reissue.

This is a divisional of application Ser. No. 08/662,845 filed Jun. 12, 1996 now U.S. Pat. No. 5,693,067 which is a divisional of application Ser. No. 08/164,398 filed Dec. 9, 1993 now U.S. Pat. No. 5,527,338, which is a continuation-in-part of application Ser. No. 07/939,296 filed Sep. 2, 1992 now U.S. Pat. No. 5,443,478. The entire text of each of the above-referenced disclosures is specifically incorporated by reference herein without disclaimer.

The present application is a continuation-in-part of co-pending application Ser. No. 07/939,296, filed on Sep. 2, 1992, and entitled "Multi-Element Intravascular Occlusion Device."

FIELD OF THE INVENTION

This invention relates to devices for placement within blood vessels for the purpose of permanent occupancy at a controlled location in the blood vessel by the device. The most frequent current use of such devices is vaso-occlusion by metallic coils delivered through a catheter to the site of occlusion.

BACKGROUND OF THE INVENTION

Endovascular use of devices to occlude blood vessels has become widespread geographically around the world and anatomically throughout the body. In endovascular therapy, the doctor attempts to produce blockage or occlusion of blood flow through a vessel in order to stop bleeding. The vessel may be either an artery or a vein. His goal may be to prevent the vessel from hemorrhaging, to limit bleeding during surgery, or to stop an abnormal blood flow pattern between blood vessels (i.e. fistulas). Devices can also be used to prevent growth of abnormal protrusions from blood vessels, such as aneurysms, by creating an occlusion within the aneurysm. This occlusion minimizes or eliminates the blood pulsations which cause abnormal stresses on the wall of the aneurysm.

Several endovascular devices have been created to accomplish these goals. These devices include "glue" thrombosis producing particles, balloons, and coils. Central to the success of the device is its ability to be precisely placed within the vessel and its ability to adhere to the vessel wall. Placement typically occurs through a catheter from a proximal position outside of a patient to a distal position within the patient. Each type of device has particular advantages and drawbacks in its efficacy and its ability to be placed.

"Glue" refers to a group of compounds that are injected into a vessel. The glue solidifies on the vessel wall. Solidification typically occurs due to exposure of the glue to electrolytes in the blood. Therefore, glue is not actually a "device" which is solid at the time of its introduction. Control of the placement of the glue is hampered due to the variability of its cure rate within the blood stream.

Thrombosis producing particles can also be introduced into the vessel to produce blockage of that vessel. These particles can be formed of various material such as polyvinyl alcohol, silicone polymer particles, glass beads, latex beads, or silk suture material. The blockage may be temporary or permanent, depending on whether and to what degree the particle is broken down in the body, resulting in recanalization of a blood vessel after occlusion. In the case of particles, blockage occurs at the point where the blood vessel diameter is smaller than the particle. Thus, if a small particle is released into a large vessel, the blood flow will carry the particle to the point where the vessel diameter diminishes to that of the particle. This is used to advantage in tumor or vascular malformation embolization, but has the disadvantage of loss of control over the point of occlusion. A balloon can be introduced within the vessel by a catheter and then inflated within the blood vessel to produce occlusion. The balloon may be permanently attached to the catheter, or it can have a valve at the point of attachment which closes when the catheter is withdrawn, detaching the balloon in position without producing subsequent deflation. With balloons permanently attached to a catheter, the blockage generally occurs at the point of placement of the tip of the catheter, such that the level of blockage is limited to the position of the tip of the catheter. That may be far into a vascular system, such as the brain, depending on the flexibility of the catheter and the skill of the operator, but the point of the occlusion is the tip of the catheter.

With detachable balloons, the method of detachment is usually traction of the balloon against the blood vessel, producing friction which causes resistance to withdrawal as the catheter is pulled out. Alternatively, balloons can also be detached by a so-called coaxial detachment system wherein detachment occurs by advancement of a larger catheter over a smaller catheter containing the balloon. The larger catheter contacts the inflated balloon preventing the withdrawal of the balloon. This permits the inner catheter to be removed from the balloon while the balloon maintains its position. However, this system is limited to larger vessels because the stiffness of both the outer and inner catheters limits their ability to advance into ever more tortuous, distal vessel portions.

Balloon occlusion devices can sometimes deflate or can even rapture the artery in which they are introduced, thus being somewhat hazardous and unpredictable. Also, balloon devices limit embolization options by producing vascular occlusion at the time of introduction. Thus, if combined embolization is desired using both particles and a more proximal occlusive device such as a balloon, the use of the balloon precludes the first use of the particles. Thus, balloons have the advantage of control over the point of occlusion but the inability to perform combined embolization while particles have the disadvantage of a lack of control over the point of occlusion.

A more recent endovascular device for small vessels, "coils," have been used for many years to present a solution to those problems in larger vessels. A coil is typically a stainless steel wire device wound such that its outer diameter matches the inner diameter of an angiographic catheter. The coil can be introduced into a catheter in a straight configuration and pushed through the catheter with a guide wire. As it exists the catheter, it can wind itself into a "coil" type configuration. The coil produces an obstacle in the blood vessel, causing blood to clot thereon. The clot blocks the blood vessel. Further development resulted in the addition of fibers of cotton or other material within the coil, increasing its propensity to cause thrombosis more quickly.

In recent years, advancements in catheter technology have allowed progressively more distal catheterizations. However, with more distal catheterizations, the stiffness of the stainless steel coil is a limitation. In response, small-diameter platinum "microcoils" were developed. These microcoils can be introduced through the catheter with a guide wire or, alternatively, be pushed by the force of an injection of water through the catheter, thus "injecting" them into the blood vessel. Such of these "coils" are actually straight, thus enabling them to follow flow in the vessel and act more like a particle. Some are curved, thus increasing the likelihood that they will not advance beyond the point of introduction. Still, all traditional coils have the disadvantage of a lack of control, insofar as they are free objects once they are introduced into the catheter. If the coils leave the catheter tip flowing in an untoward direction or if the catheter tip moves at the time of introduction, the physician has no control over this undesirable situation or ability to recall or reposition the coil. Thus, their successful placement is extremely depending on the skills of the surgeon/radiologist placing them.

Additionally, coils often fail to produce complete occlusion of the vessel. Because of continued canalization or recanalization, blood flow through the partially occluded vessel continues. Also, because of the size of the coils, complete occlusion of the vessel often requires that multiple coils be placed to ensure occlusion. The additional coils add expense and lengthen the time necessary to complete the procedure.

Therefore, a need exists for a more widely applicable intravascular occlusion device. Such an occlusion device should produce the greatest amount of occlusion with the most flexible device. The occlusion device can even be a hybrid combination of other such devices. Given the time and expense involved in using intravascular coils, this new device should save substantial time and money via the use of fewer units to achieve the desired end. A need also exists for a device which creates complete occlusion of the vessel immediately. Such device could be used in situation where distal thromboembolization would be unacceptable.

SUMMARY OF THE INVENTION

The present invention relates to a multi-element intravascular occlusion device comprising at least one lead element attached to at least one anchoring element by at least one fiber. The lead element can be either a particle or a coil. Likewise, the anchoring element can be either a particle or a coil. Interference of flow created by the fiber linking the elements will exceed the sum of the effect of the separate elements. Instead of clotting on a single particle or coil, the blood clots around each part of the device. The resulting occlusion is deeper and thus decreases the risk of continued canalization or recanalization.

The present invention will also save time and money. Instead of requiring the placement of several coils or particles to achieve occlusion, the device allows a more rapid occlusion with fewer deployments. The device can be placed into a vessel by conventional means to create thrombosis and thereby occlude continued blood flow.

Either the lead element or anchoring element can be made of almost any material and can be almost any shape. For example, current occlusive particles include glass beads and protein particles to produce occlusion. The particles come in several different sizes and shapes. A coil can be made of stainless steel, platinum, or other suitable material. Like the particles, the coils are also available in varying shapes and sizes. The most desirable material, shape and size for the device will depend on the individual circumstances of the desired occlusion. Typically, the size will be limited by the catheter used to place the occlusion device.

Once the occlusion device exists the catheter, the device can flow downstream until the anchoring element lodges against the vessel wall. Typically, the anchoring element will lodge at that point where its circumference is greater than that of the vessel wall. In an alternate embodiment, the anchoring element can have forward prongs which penetrate the vessel wall, thereby fixing the position of the anchoring element. The lead element flows to a position distal to the anchoring element. Thus, the lead element will usually be somewhat smaller than the anchoring element.

The lead element is connected to the anchoring element by at least one fiber. The fiber can be either metallic or nonmetallic. It can be attached to the lead and anchoring elements chemically or mechanically. The length of the at least one fiber can determine the distance the lead element can flow downstream from the anchoring element. In a preferred embodiment, several fibers are used. The fibers can be of the same or different lengths. Likewise, the stiffness of the fiber can be controlled to limit the positioning of the lead element. For example, a doctor may use a device with flexible synthetic fibers if the location of the desired occlusion is in a blood vessel which has sharp turns. In other cases, several stiff fibers made of steel may be needed to prevent the lead element from moving. In some cases, the circumstances may even require a fiber capable of elongation.

In an alternate embodiment, a single anchoring element is used with several lead elements. The lead elements can be arranged sequentially, or can be attached to the anchoring element as separate branches. In fact, one embodiment could comprise a single anchoring element with two branches extending therefrom, wherein one branch comprises a single lead element while the other branch comprises several lead elements attached sequentially. In another embodiment, two or more anchoring elements might be used with a single lead element. In another embodiment, several fibers can be intertwined to create a lead element.

In another embodiment, the lead element could be a pharmacologic or other bioactive element. This pharmacological element could even be a clot dissolving drug.

In another embodiment, the lead element out of the catheter could be used to anchor the intravascular device to the vessel wall. The "anchor element" would, therefore, not anchor the device at all but flow downstream of the lead element.

In another embodiment, the intravascular device would comprise a lead element and a trail element connected by at least one fiber. A plurality of expansion members umbrella out from device near the lead element. In fact the expansion members can represent the lead element. Each expansion member is attached to its adjacent members by a fabric. The expansion members expand outward when the device exists the catheter and form an umbrella. The tips of the expansion members can be bent forward to improve their ability to engage the vessel wall. This embodiment creates acute, complete occlusion of the vessel. Thrombosis is not required to fill in the spaces between elements of the device, as is the case with traditional coils.

In another embodiment, the trailing element may function only to assist in detachment of the lead element. Alternatively, the trailing element may even detach from the lead element allowing more precise localization of the lead element without requiring that the trailing element be deposited in the vessel with the lead element.

BRIEF DESCRIPTION OF THE DRAWINGS

For a more complete understanding of the present invention, and for further details and advantages thereof, reference is now made to the following Detailed Description taken in conjunction with the accompanying drawings, in which.

DETAILED DESCRIPTION OF THE INVENTION

Figure 1:
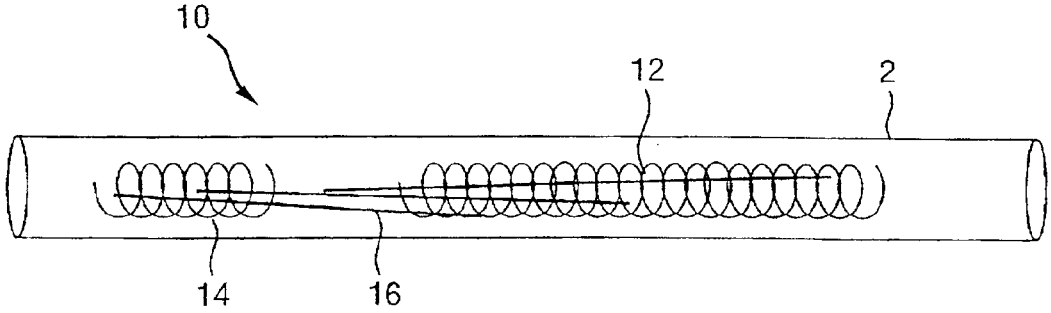
FIG. 1 provides a perspective view of the device compressed within an introducing catheter.
Figure 2:
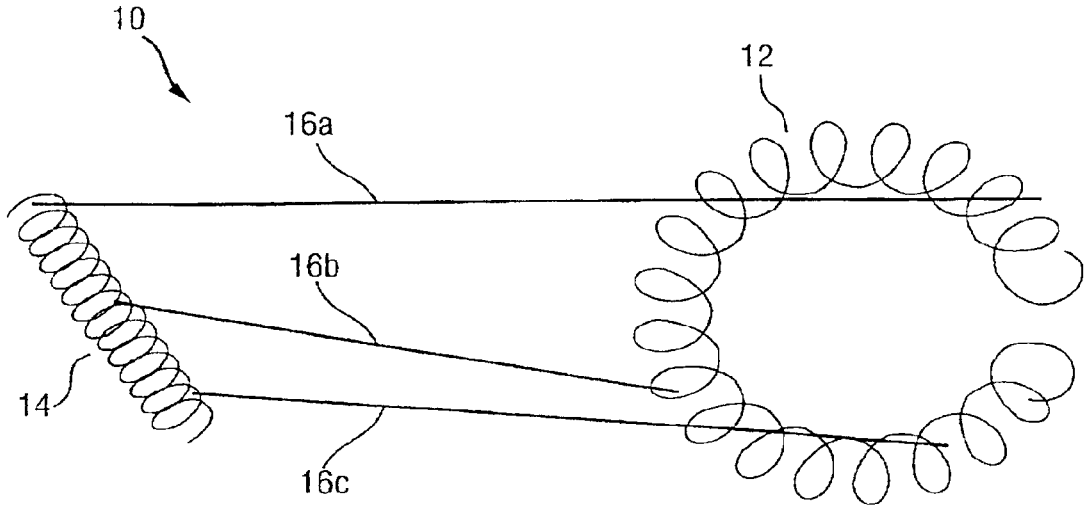
FIG. 2 shows a perspective view of a first embodiment deployed wherein the lead element is a coil.

The present invention relates to a multi-element intravascular occlusion device which overcomes many of the disadvantages in the prior art. FIGS. 1 and 2 illustrate a first embodiment of the device 10 in both a compressed and a deployed configuration. The device 10 comprises an anchoring element 12 and a lead element 14 connected by fibers 16, wherein both elements are coils. An introducing catheter 2 is used to place the device 10 into a blood vessel. As the device 10 is placed in the vessel, the anchoring element 12 deploys and lodges against the wall of the vessel. The blood flow carries the lead element 14 distally up to the length of the fibers 16. Blood clots form around the anchoring element 12, the fibers 16 and the lead element 14 to occlude blood flow through the vessel.

The potential shape of the coils are unlimited. Currently, numerous configurations of coils exist. For example, a "Gianturco coil" by Cook, Inc. includes multiple turns into a spring-like shape. Another coil, the Flower coil by Target Therapeutics, includes multiple turns which are offset from one another. Hilal coils, also manufactured by Cook, Inc., include either single turns or straight configurations of various lengths or diameters. It is anticipated, however, that the initial configuration of the device 10 will contain a curved anchoring element 12, as shown.

Though the size of the lead element 14 will vary, it will generally be smaller than that of the anchoring element 12. The smaller the size of the lead element 14 relative to the anchoring element 12, the more likely it is that the lead element will be carried distally by the blood flow. Unlike the curved anchoring element 12, the lead element 14 in the anticipated initial configuration of the device 10 will comprise a straight cell as shown.

A plurality of fibers 16a, 16b, 16c serve as a means for connecting the anchoring element 12 and the lead element 14. Fibers 16 are typically between 3 and 30 mm in length. However, they may be any length suitable for the application. Moreover, the fiber 16 may be capable of elongation. The material used for the fiber 16 can affect the behavior of the lead element 14. For some uses, the fibers 16 should be made of metal. In other applications nonmetallic fibers 16 are preferable. The desired behavior of the device 10 and factors such as strength, flexibility, or bonding to the other elements will determine the material used.

The attachment of the fibers 16a, 16b, 16c to the anchoring element 12 and the lead element 14 may be achieved by solid or mechanical means. Solid attachment may be achieved by use of solder or glue materials or by melding or fusion of the two. Mechanical attachment may be achieved by tying or twisting a fiber 16 onto the other elements. The attachment of the elements will be a function, to some extent, of the desired application.

Figure 3:
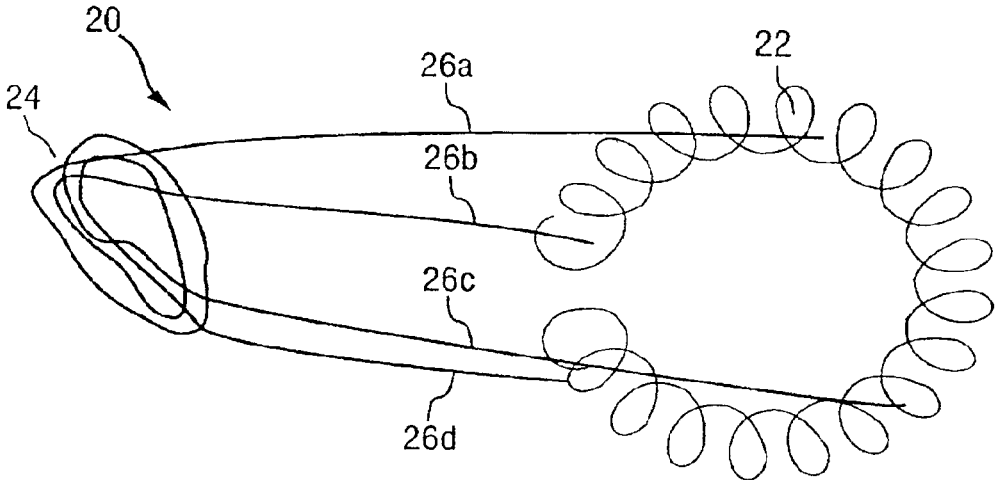
FIG. 3 gives a perspective view of a second embodiment wherein the lead element is comprised of intermeshing fibers.

FIG. 3 illustrates occlusion device 20 which represents a second embodiment of the present invention. The occlusion device 20 comprises an anchoring element 22 and a lead element 24 connected by fibers 26a, 26b, 26c, 26d. The anchoring element 22 comprises a coil similar to that shown in FIG. 2. The lead element 24, however, is formed by an intermeshing of fibers 26. The distance between the lead element 24 and the anchoring element 22 can be controlled both by the length of the fibers 26 and the location at which the fibers are intermeshed. The fibers 26 may be held together by a knot, or by some other means such as glue.

The lead element 24, as illustrated, acts like a thrombosis producing particle. Therefore, the lead element 24 can be any other thrombosis producing particle such as polyvinyl alcohol, silicone polymer, protein particles, glass beads, latex beads, or silk suture material.

Figure 4:
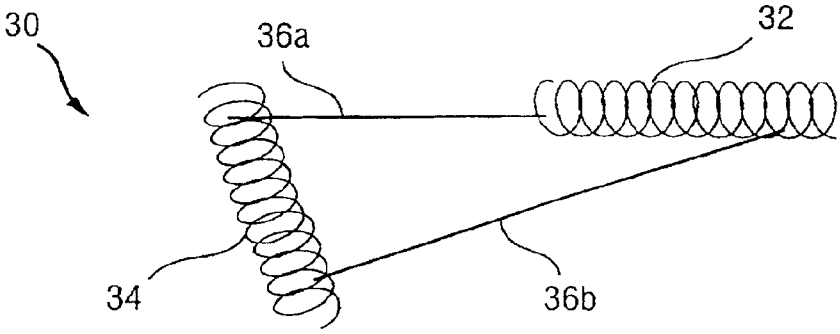
FIG. 4 provides a perspective view of a third embodiment in which the lead element and the anchoring elements are attached by fibers with different lengths.
Figure 5:
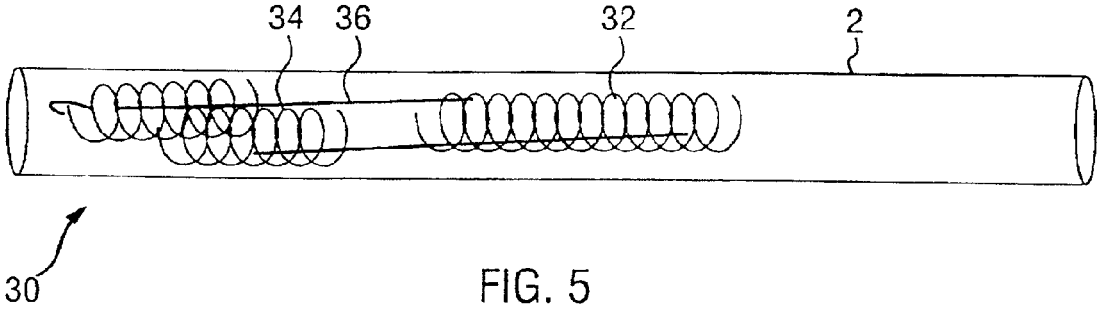
FIG. 5 illustrates a perspective view of the device in FIG. 4 contained within an introducing catheter.

FIGS. 4 and 5 illustrate occlusion device 20 which represents a third embodiment of the present invention. Again, the occlusion device 30 comprises an anchoring element 32 and a lead element 34 connected by two fibers 36a, 36b. Both the lead and anchoring elements 32, 34, are shown as straight coils. As shown, fiber 36a is shorter than fiber 36b. Both fibers can be attached to any part of either element. Fibers 36a and 36b are attached to opposite ends of each coil. By varying the numbers of fibers 36 and where they attach the other elements, the behavior of the lead element 34 can be altered.

The mechanism of delivery for device 10, 20, 30 can incorporate any of the currently available mechanisms. These include either mechanical pushing of the coil through the introducing catheter 2 by a guide wire, injection of the coil using saline or other liquid to wash it from the introducing catheter 2, or use of a detachment apparatus which allows for controlled delivery or withdrawal. Utilization of the system will most frequently occur via a transfemoral catheterization, either arterial or venous. An angiographic catheter will be placed such that its tip is near the desired deployment location. In some cases, this will involve a coaxial catheterization. For instance, in cerebral embolization it is common to place an catheter from the femoral approach into the carotid or vertebral artery, from there, a second smaller catheter is inserted by way of the angiographic catheter and advanced to a point within the brain near the pathology, and the embolization is conducted through this smaller catheter. In these situations, that smaller catheter becomes the introducing catheter 2 for purposes of this application, since it is the most distally placed catheter through which the device will be introduced.

Following angiographic verification of placement of the introducing catheter 2, the device will be introduced into the hub of the introducer. Following introduction, the device is advanced until it can be seen under fluoroscopy that it is exiting the introducing catheter 2. With a free-standing coil, the device's exit from the introducing catheter 2 will result in final placement. With a detachable device, the detachment is performed when the device is observed to have exited the introducing catheter 2 completely and is an appropriate position and configuration. Since the detachment of the device and subsequent removal of the detaching system do not require removal of the introducing catheter 2, the same process may be repeated if additional devices are required.

A multi-element occlusion device may be more difficult to retract. Since the lead element 14, 24, 34 can already be free of the introducing catheter 2, it may become caught at the time of attempted retraction. Variations in design may be used in situations wherein database devices are used or in which a potential need for retraction may be anticipated. Though devices now exist which are designed for coil retrieval after placement, it is anticipated that deposition of this device into the vascular space is permanent. The intent is to induce permanent occlusion of a blood vessel or cavity or permanent obliteration or occupation of a space.

Figure 6:
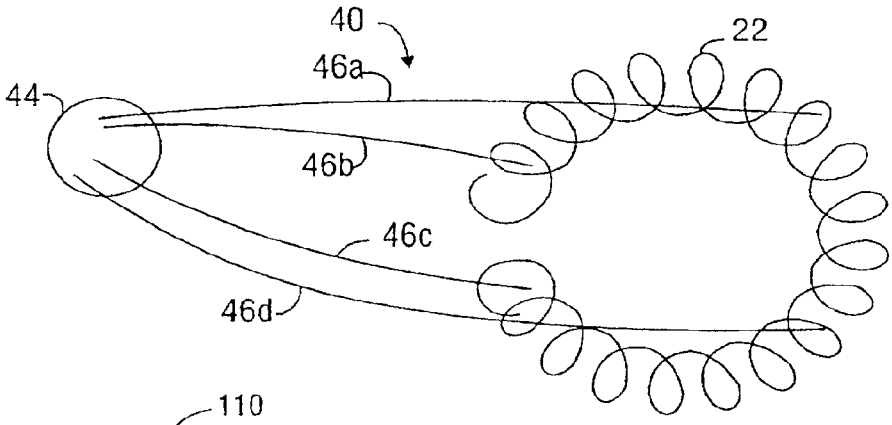
FIG. 6 provides a perspective view of the device wherein the lead element is a pharmacologic or other bioactive element.

FIG. 6 provides a perspective view of an intravascular device 40 wherein the lead element 44 is a pharmacologic or other bioactive element. The lead element can be mechanically or chemically attached to the at least one fiber leading 46 to the anchoring element 42. The pharmacologic element could even be a clot dissolving drug. The trailing element can be sized to lodge at a particular point in a vessel, thus allowing controlled placement of the pharmacologic element or other bioactive element.

Figure 7:
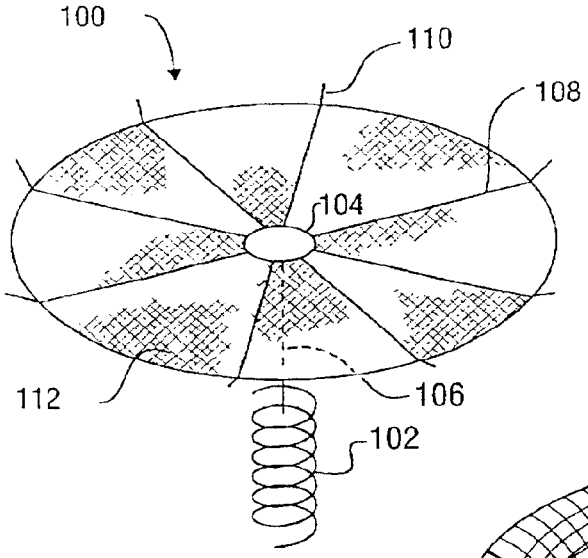
FIG. 7 provides a perspective view of another embodiment of the device with a lead element and a trailing element connected by at least one fiber and wherein the lead element is further connected to a skeleton which supports a flat fabric umbrella.
Figure 10:
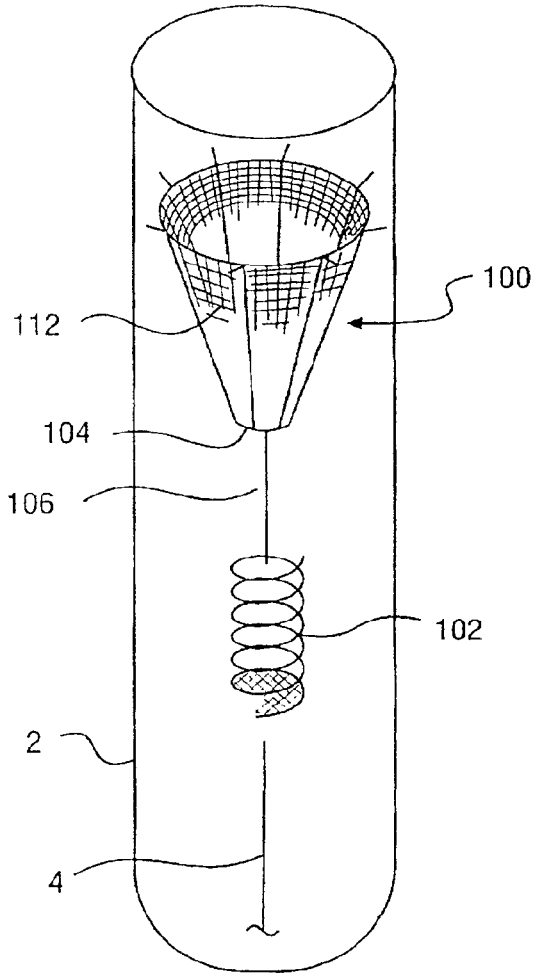
FIG. 10 illustrates the umbrella intravascular device of FIG. 7 loaded in a catheter.
Figure 11:
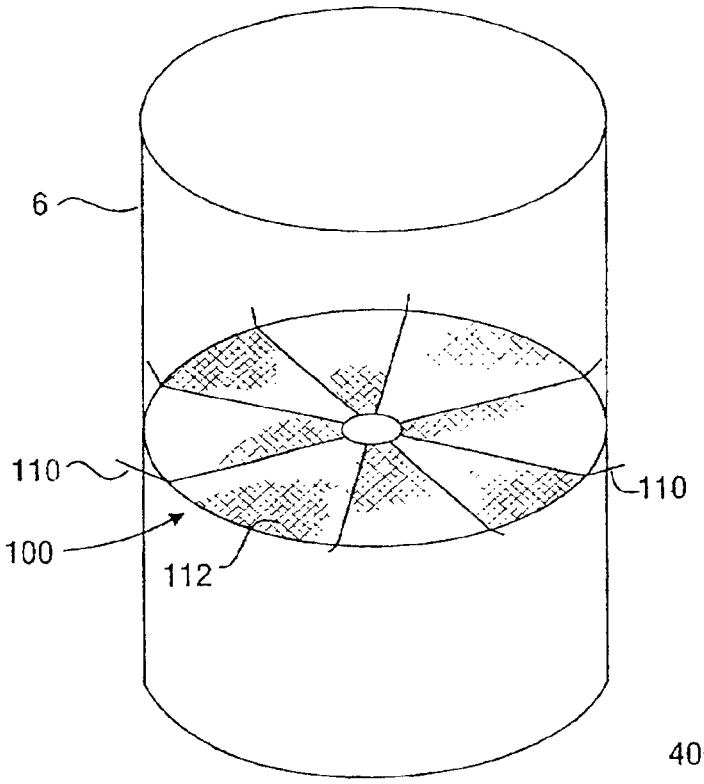
FIG. 11 illustrates the umbrella intravascular device of FIG. 7 deployed in and engaged to the vessel.

Referring to FIGS. 7, 10 and 11, an "umbrella" embodiment 100 of an intravascular device comprises a lead element 104 connected to a trailing element 102 by at least one fiber 106. The lead element 104 is further connected to a plurality of expansion members 108 which supports a fabric umbrella 112. FIG. 7 illustrates the intravascular device 100 in a deployed state as seen from below. The expansion members 108 of the intravascular device are arranged in this iteration in a radially projecting pattern from the lead element 104. The lead element 104 can be another type of intravascular device, such as a coil, or it can act merely as an attachment point as with the illustrated embodiment. The space between the expansion members 108 is filled by a woven material 112 which fills it completely and stops flow from progressing from a point proximal to the coil to a point distal to the coil. The tips 110 of each expansion member are typically bent forward. This allows the tips to engage the vessel wall.

The fiber 106 used to connect the leading and trailing element can be of any suitable length. The fabric between the expansion members is any suitable material which can block the flow of fluid, particularly blood, therethrough. In a preferred embodiment, the fabric is Dacron. The trailing element 102 can be a coil, fiber, or other suitable device. A coil is illustrated. A guide wire 4 can connect to the trailing element 102 at point 102a, or the guide wire can merely push the device 100 from a catheter 2. The trailing element 102 may be small or nonexistent as a requirement of the coil design and are included as a potential mechanism to attach the coil to an introducer or detachment apparatus. The fibers may be arranged radially, as shown here, or in another pattern such that structural integrity is preserved to maintain the functionality of the device as an occlusive tool. The tips of the expansion members may be sharp or blunt at their tips, to allow maintenance of placement by penetration of the vessel wall or by friction against the vessel wall.

FIG. 10 illustrates the device 100 in a compressed state within a catheter 2. The introducer 4 is shown adjacent to the trailing element. The introducer can be used to push the device 100 from the catheter. Different configurations of the umbrella device can be collapsed in the catheter in different ways. FIG. 11 illustrates the assembly following deployment, as seen from above, to demonstrate the occupation of the vessel lumen 6 by the deployed device 100. The connecting fiber 106 and attaching coil 102 remain attached to the umbrella 110, 112 but are not illustrated here, since this perspective is from above. Note contact of the prongs of the tips 110 of expansion members 108 with the vessel wall 6. This contact may be simply frictional via blunt contact of the prongs with the vessel wall or may involve shallow penetration of the vessel wall via sharper prongs. In either case, the prongs provide points of stabilization of placement of the device to help prevent migration following deployment. Embodiment 100 presents a flat surface to the flow of blood.

Figure 8:
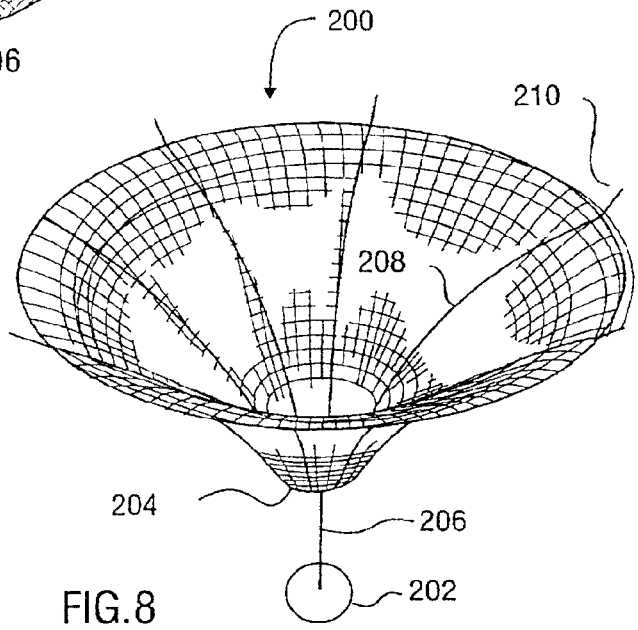
FIG. 8 provides a side view of another embodiment in which the fibers from a convex umbrella portion of the intravascular device.

FIG. 8 provides a sectional view of another embodiment of the intravascular device 200. The expansion members 208 extend from a lead element 204. The lead element 204 is connect to a trailing element 202 by at least one fiber 206. The expansion members support a fabric web, as with the previous embodiment. However, the expansion members 208 are curved to present a convex surface to the flow of blood. As with the previous embodiment, after the intravascular device lodges in the vessel, blood clots along the fiber(s) 206 and the leading and trailing elements. The fabric between the expansion members block the flow of blood and also prevent distal thromboembolizaiton.

Figure 9:
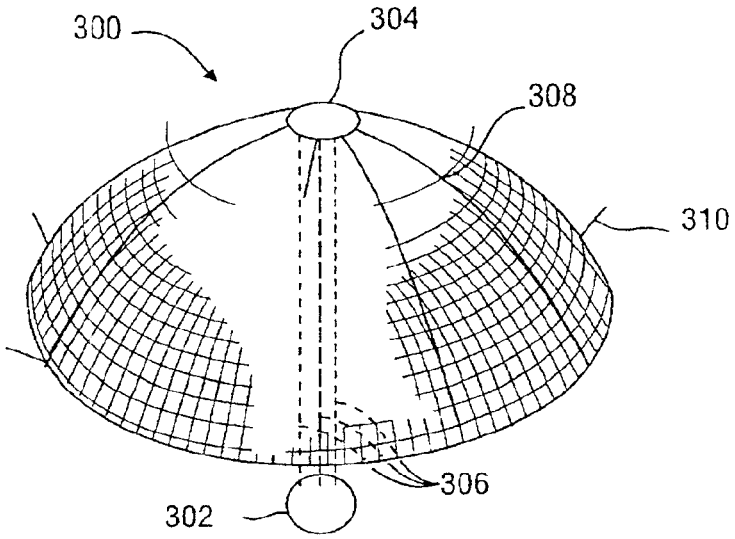
FIG. 9 illustrates a side view of another embodiment in which the fibers are used to form a concave umbrella intravascular device.

FIG. 9 illustrates a side view of another embodiment of the umbrella intravascular device 300. The device is comprised of a lead element 304 connected to a trailing element 302 by at least one fiber 306. The lead element acts as a hub for a plurality of expansion members 308 with tips 310. The device 300 is shown in a compressed state loaded in a catheter 2. A guide wire 4 contacts the trailing element 302. The introducer can push the device 300 into the blood flow where the expansion members 308 expand. The device flows downstream, if even a small distance. It lodges at a point where the vessel diameter is smaller than the device diameter. Alternatively, the device 300 can be detached by -coaxial detachment. The trailing element 302 is lightly attached to the guide wire 4 by mechanical or chemical means. The device 300 is advanced beyond the catheter 2 at which time it expands. The guide wire is then pulled back, bringing the attached device 300 into contact with the tip of the catheter 2. By pulling the guide wire 2 further, the attachment between the trailing element 302 and the guide wire 4 is broken and the device 300 can flow downstream as indicated by the arrows A. Embodiment 302 presents a concave surface to the blood flow.

It is believed that a convex umbrella is the most stable iteration of the umbrella intravascular devices 100, 200, 300. Blood flow pushing against the concave configuration could collapse it distally and make embolization more likely. The convex embodiment, however, should tend to expand against the walls of the blood vessel as blood pushes against it, thus causing it to anchor even more tightly.

Figure 12:
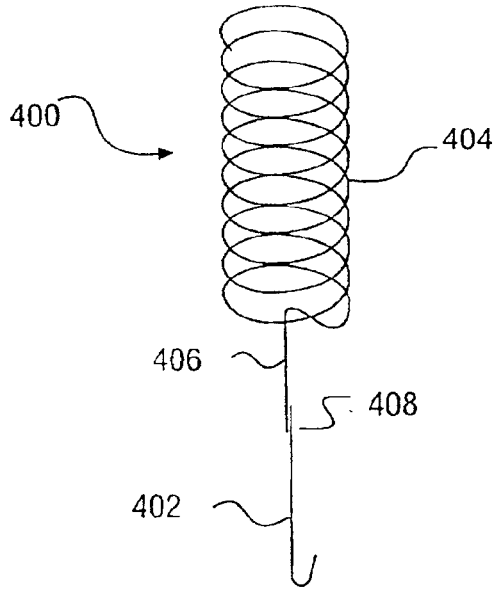
FIG. 12 illustrates another embodiment in which the lead element is detached from the trailing element at the time of intravascular deposition, with the trailing element remaining behind with the introducer apparatus.

Referring to FIG. 12, an intravascular device 400 uses a trailing element 402 which detaches from the remaining portion of the coil at point 408, along with a detachment apparatus (not shown). It serves only to assist in the detachment and does not function as a permanent member of the device within the tubular structure (e.g. blood vessel). Since the detachment apparatus is completely separate from the "coil", re-use of the detachment apparatus on multiple coils is possible. In this particular device shown, the detachment apparatus would have a loop on the end which would engage a hook on the proximal part of the coil, pulling it back into the catheter to the point where the detachment portion was near the end of the catheter. When the coil then was introduced to the detachment point, further retraction on the detachment apparatus core would cause detachment of the proximal from the distal component of the intravascular device.

The most immediately obvious application of this device is to use to occlude large vascular lumens which require placement of multiple currently commercially available coils. Other applications may ensure to occlude lumens of other tubular structures, such as veins or fallopian tubes. No currently available coil acts via an immediate, completely occlusive action as it is the case with this intravascular device. Detachable balloons are the most analogue in that regard, but their construction and method of use is radically different from that of the umbrella intravascular device. Specifically, balloons do not create thrombosis upstream from their location.

The material from which the distal element are constructed need not be limited. For some applications, filaments of synthetic materials may be more appropriate for use as the skeleton fibers, owing to increased structural integrity flexibility or stiffness, or other physical qualities which those materials may impart. For other applications, metallic wire may be applicable. Currently, wires of stainless steel, platinum, tungsten, and gold and other devices of cobalt and other metals are used in medical applications. Factors such as strength, flexibility, or bonding to the other elements may favor one metal over another also.

The attachment of the elements to one another will be a function, to some extent, of the desired application. In some instances, a more rigid web of material may be desired to bridge between expansion members. In other instances, a more flexible attachment may be desired in order to allow the umbrella to collapse more completely or to navigate more tortuous tubular channels.

Attachment of the elements to one another may be achieved by solid or mechanical means. Solid attachment may be achieved by use of solder or glue materials or by melding or fusion of the two (welding or melting one to the other). Alternatively, a collar of wire or other material may be used to connect fibers to each other or to connect the skeleton to the material forming the umbrella.

The distal, occlusive element is anticipated initially to be connected to the proximal element by at least one connecting wire or fiber such that the distal element is carried a short distance distally. Using a detachment system for introduction, the presence of the connecting fiber would allow a loose placement of the umbrella from the introducer, thus allowing the physician performing the placement to test the stability of the deployment and to assure that the risk of embolization of the device is minimal -prior to ultimate detachment and permanent placement. Thus, the connecting fiber and attaching coil combination allow assurance that the occlusive umbrella element is stable in its placement prior to withdrawal of the introducer and detachment apparatus.

The lead and trail elements can be coils as described above. Typically, if coils are used, the deployed coils can be stainless steel coils, larger platinum coils, or coils constructed of nonmetallic materials proximal to the umbrella component. These may be desirable to enhance the detachment or stability of placement of the device. This modification of the deployable coil may permit utilization of materials which are designed to maximize thrombosis or achieve some other therapeutic aim such as vascular sclerosis.

As with earlier embodiments, utilization of the umbrella intravascular device will most frequently occur via a transfemoral catheterization, either arterial or venous. An angiographic catheter (referred to in FIG. 2 as catheter 8) will be placed such that its tip is near the desired deployment location. In some cases, this will involve a coaxial catheterization. For instance, in cerebral embolizations it is common to place an introducer catheter from the femoral approach into the carotid or vertebral artery. From there, a second smaller catheter is inserted by way of the angiographic catheter and advanced to a point within the brain near the pathology, and the embolization is conducted through this smaller catheter. In these situations, that smaller catheter becomes the introducer catheter for purposes of this application, since it is the most distally placed catheter through which the device will be introduced.

Following angiographic verification of placement of the introducer catheter, the system will be introduced into the hub of the introducer. It is anticipated that an assisting device for the introduction of the system will be necessary, as described above. Again, however, different designs to achieve this are possible and the design of the assisting device is not critical to this application. Following introduction, the coil is advanced within the introducer until it can be seen under fluoroscopy to be exiting the introducer. If it is a free-standing coil, its exit from the introducer catheter will result in final placement. If it is a detachable device, when the device is observed to have exited the introducer completely and to lie in an appropriately stable position and configuration, the detachment is performed.

Although preferred embodiments of the invention have been described in the foregoing Detailed Description and illustrated in the accompanying drawings, it will be understood that the invention is not limited to the embodiments disclosed, but is capable of numerous rearrangements, modifications, and substitutions of parts and elements without departing from the spirit of the invention. Accordingly, the present invention is intended to encompass such rearrangements, modifications, and substitutions of parts and elements as fall within the scope of the invention.

I claim:

[1. An intravascular device for use with a catheter having a detachment apparatus, said device comprising:

at least one lead element; and a trailing element detachably interconnected to at least one said lead element, said trailing element adapted for attachment to said detachment apparatus;

wherein said at least one lead element is structured to cause occlusion of a vessel.]

[2. The intravascular device of claim 1, wherein said at least one lead element comprises a material capable of producing thrombosis.]

[3. The intravascular device of claim 1, wherein said at least one lead element comprises an expansible element.]

[4. The intravascular device of claim 1, wherein said at least one lead element comprises a particle.]

[5. The intravascular device of claim 1, wherein said at least one lead element comprises a coil.]

[6. The intravascular device of claim 1, wherein said trailing element is chemically detachable from said at least one lead element.]

[7. The intravascular device of claim 1, wherein said trailing element is mechanically detachable from said at least one lead element.]

[8. The intravascular device of claim 1, wherein said at least one lead element functions as an anchoring element.]

[9. The intravascular device of claim 1, further comprising a fiber detachably interconnecting said at least one lead element and said trailing element.]

[10. The intravascular device of claim 1, wherein the end of said detachment apparatus has the shape of a loop, and wherein said trailing element comprises a hook adapted to engage said loop.]

[11. The intravascular device claim 10, wherein said at least one lead element comprises a coil.]

[12. An intravascular device comprising:

at least one lead element;

a trailing element; and a fiber detachably interconnecting the trailing element to said at least one lead element;

wherein said at least one lead element is capable of causing occlusion of a vessel.]

[13. The intravascular device of claim 12, wherein said at least one lead element comprises a material capable of producing thrombosis.]

[14. The intravascular device of claim 12, wherein said at least one lead element comprises a coil.]

[15. The intravascular device of claim 12, wherein said at least one lead element functions as an anchoring element.]

[16. An intravascular device for use with a catheter having a detachment apparatus, said device comprising:

at least one lead element;

a trailing element; and a fiber detachably interconnecting the trailing element to said at least one lead element;

wherein said at least one lead element is capable of causing occlusion of a vessel, and wherein said trailing element is adapted for attachment to said detachment apparatus.]

[17. The intravascular device of claim 16, wherein said at least one lead element comprises a material capable of producing thrombosis.]

[18. The intravascular device of claim 16, wherein said at least one lead element comprises a coil.]

[19. The intravascular device of claim 16, wherein said at least one lead element functions as an anchoring element.]

[20. The intravascular device of claim 16, wherein the end of said detachment apparatus has the shape of a loop, and wherein said trailing element comprises a hook adapted to engage said loop.]

[21. The intravascular device of claim 20, wherein said at least one lead element comprises a coil.]

*22. A method for producing occlusion of a vessel or an aneurysm, including:*

*providing an intravascular device having a lead element, and a trailing element connected by a non-metallic member to the lead element;*

*providing a detachment apparatus engaging the trailing element of the intravascular device;*

*providing an introducing catheter with a distal end;*

*inserting the introducing catheter into the vessel or aneurysm such that the distal end is adjacent to a desired deployment location;*

*inserting the intravascular device into the introducing catheter;*

*positioning the intravascular device at a position to occlude at least a portion of the vessel or the aneurysm; and*

*disengaging the intravascular device from the detachment apparatus.*

*23. The method of claim 22, wherein the non-metallic member is a synthetic member.*

*24. A method for producing occlusion of a vessel or an aneurysm, including;*

*providing an intravascular device having a lead element, and a non-spherical trailing element connected to the lead element;*

*providing a detachment apparatus engaging the non-spherical trailing element of the intravascular device;*

*providing an introducing catheter with a distal end;*

*inserting the introducing catheter into the vessel or aneurysm such that the distal end is near a desired deployment location;*

*inserting the intravascular device into the introducing catheter;*

*positioning the intravascular device to occlude at least a portion of the vessel or the aneurysm; and*

*disengaging the intravascular device from the detachment apparatus.*

*25. The method of claim 24, wherein the lead element is connected to the non-spherical trailing element by a non-metallic member.*

*26. The method of claim 25, wherein the non-metallic member is a synthetic member.*

*27. A method for producing occlusion of a vessel or an aneurysm, including:*

*providing an intravascular device having a bioactive lead element, and a trailing element connected to the bioactive lead element;*

*providing a detachment apparatus engaging the trailing element of the intravascular device;*

*providing an introducing catheter with a distal end;*

*inserting the introducing catheter into the vessel or aneurysm such that the distal end is near a desired deployment location;*

*inserting the intravascular device into the introducing catheter;*

*positioning the intravascular device to occlude at least a portion of the vessel or the aneurysm; and*

*disengaging the intravascular device from the detachment apparatus.*

*28. The method of claim 27, wherein the bioactive lead element is connected to the trailing element by a non-metallic member.*

*29. A method for producing occlusion of a vessel or an aneurysm, including:*

*providing an intravascular device having a lead element, and a trailing element comprising a coil connected to the lead element;*

*providing a detachment apparatus engaging the trailing element of the intravascular device;*

*providing an introducing catheter with a distal end;*

*inserting the introducing catheter into the vessel or aneurysm such that the distal end is near a desired deployment location;*

*inserting the intravascular device into the introducing catheter;*

*positioning the intravascular device to occlude at least a portion of the vessel or the aneurysm; and*

*disengaging the intravascular device from the detachment apparatus.*

*30. The method of claim 29, wherein the lead element is connected to the trailing element by a non-metallic member.*

*31. The method of claim 30, wherein the non-metallic member is a synthetic member.*

*32. A method for producing occlusion of a vessel or an aneurysm, including:*

*providing an intravascular device having a lead element, and a trailing element connected to the lead element, the trailing element being configured to anchor the intravascular device within the vessel or aneurysm;*

*providing a detachment apparatus engaging the trailing element of the intravascular device;*

*providing an introducing catheter with a distal end;* inserting the introducing catheter into the vessel or aneurysm such that the distal end is near a desired deployment location;

inserting the intravascular device into the introducing catheter;

positioning the intravascular device to go occlude at least a portion of the vessel or the aneurysm; and disengaging the intravascular device from the detachment apparatus.

*33. The method of claim 32, wherein the lead element is connected to the trailing element by a non-metallic member.*

*34. The method of claim 33, wherein the non-metallic member is a synthetic member.*

* * * * *

UNITED STATES PATENT AND TRADEMARK OFFICE

CERTIFICATE OF CORRECTION

PATENT NO. : RE 38,972 E
APPLICATION NO. : 09/909662
DATED : February 7, 2006
INVENTOR(S) : Phillip D. Purdy It is certified that error appears in the above-identified patent and that said Letters Patent is hereby corrected as shown below:

In claim 32, column 14, lines 5- 13, please delete:

"inserting the introducing catheter into the vessel or aneurysm such that the distal end is near a desired deployment location;
inserting the intravascular device into the introducing catheter;
positioning the intravascular device to go occlude at least a protion of the vessel or the aneurysm; and
disengaging the intravascular device from the detachment apparatus"

and insert:

--*inserting the introducing catheter into the vessel or aneurysm such that the distal end is near a desired deployment location;*
*inserting the intravascular device into the introducing catheter;*
*positioning the intravascular device to occlude at least a portion of the vessel of the aneurysm; and*
*disengaging the intravascular device from the detachment apparatus*--.

Signed and Sealed this

Thirtieth Day of January, 2007

JON W. DUDAS
*Director of the United States Patent and Trademark Office*